(12) United States Patent
Walter et al.

(10) Patent No.: US 8,822,380 B2
(45) Date of Patent: Sep. 2, 2014

(54) HERBICIDAL COMPOSITION

(75) Inventors: James Walter, West Chester, PA (US); Frank Robert Walls, Jr., Goldsboro, NC (US)

(73) Assignee: FMC Corporation, Philadelphia, PA (US)

( * ) Notice: Subject to any disclaimer, the term of this patent is extended or adjusted under 35 U.S.C. 154(b) by 523 days.

(21) Appl. No.: 12/328,430

(22) Filed: Dec. 4, 2008

(65) Prior Publication Data
US 2009/0156401 A1    Jun. 18, 2009

Related U.S. Application Data

(60) Provisional application No. 61/007,316, filed on Dec. 12, 2007.

(51) Int. Cl.
*A01N 63/00* (2006.01)
*A01N 43/40* (2006.01)
*A01N 43/42* (2006.01)
*A01N 43/00* (2006.01)
*A01N 43/653* (2006.01)

(52) U.S. Cl.
CPC .................................. *A01N 43/653* (2013.01)
USPC ........... 504/118; 504/130; 504/139; 504/247; 504/273

(58) Field of Classification Search
USPC .......................... 504/139, 118, 130, 247, 273
See application file for complete search history.

(56) References Cited

U.S. PATENT DOCUMENTS

| 4,497,651 A | 2/1985 | Hagen et al. |
| 4,818,275 A | 4/1989 | Theodoridis |
| 6,849,579 B2 | 2/2005 | Armbruster et al. |
| 7,144,842 B2 | 12/2006 | Kawasaki et al. |
| 8,119,567 B2 | 2/2012 | Hashman et al. |

FOREIGN PATENT DOCUMENTS

WO    WO 03/024224 A2    3/2003

OTHER PUBLICATIONS

McDonald, S.J., Early Post-emergent Control of Smooth Crabgrass and Thin Paspalum with Tank-mixes of Various Herbicides. [online]. Turfgrass Disease Solutions, 2007 [retrieved on Jan. 21, 2011]. Retrieved from the Internet: http://turfgrassdiseasesolutions.com/sys/docs/31/Paspalum-Crab%20Control_2007%20PCC.pdf.*

* cited by examiner

*Primary Examiner* — Sue Liu
*Assistant Examiner* — Andriae M Holt
(74) *Attorney, Agent, or Firm* — FMC Corporation

(57) ABSTRACT

The present invention provides a method for post-emergence selective weed control in turf sites by applying an herbicidal composition comprising sulfentrazone and quinclorac to a locus where weeds are present.

3 Claims, No Drawings

HERBICIDAL COMPOSITION

This application claims the benefit of U.S. Provisional Application No. 61/007,316 filed Dec. 12, 2007.

FIELD OF THE INVENTION

This invention relates to a method for post-emergence selective weed control in turf sites by applying a composition comprising a mixture of N-[2,4-dichloro-5-[4-(difluoromethyl)-4,5-dihydro-3-methyl-5-oxo-1H- 1,2,4-triazol-1-yl]phenyl]methanesulfonamide and 3,7-dichloro-8-quinolinecarboxylic acid to a locus where weeds are present.

BACKGROUND OF THE INVENTION

U.S. Pat. No. 4,497,651 discloses Dichloroquinoline Derivatives for use as Herbicides. U.S. Pat. No. 4,818,275 discloses Herbicidal Aryl Triazolinones.

U.S. Pat. No. 6,849,579 discloses and claims a selective synergistic post-emergent herbicidal composition comprising quinclorac herbicide and a selective protox herbicidal inhibitor in which the composition when applied to control unwanted vegetation contains sufficient amounts of the quinclorac and the protox inhibitor to supply from about 0.1 to about 1 lb/acre of quinclorac and from about 0.005 to about 0.06 lb/acre of the protox herbicidal inhibitor.

The use of herbicides to control weeds in turf is well known. There are two types of herbicide applications, pre-emergence herbicides prevent weed seeds from germinating or emerging and post-emergence herbicides that kill emerged and actively growing plants.

Pre-emergence turf herbicides are generally more effective, but must be applied early in the season before annual weed seeds germinate. In order to provide season-long control most pre-emergent herbicides need to be reapplied six to eight weeks after the initial application. An infestation of annual weeds either over an entire site or in localized areas of a site cannot be confirmed so early in the season, the time and expense of treating turf with pre-emergence applications of herbicides may not be needed.

Post-emergence turf herbicides are used to control weeds after germination and emergence from the soil. The benefit of using a post-emergence turf herbicide for weed control is that it is used only where an infestation is present. Some of the most common post-emergence turf herbicides must be reapplied several times, for example, organic arsenicals which include MAMA (monosodium methanearsonate), and DSMA (disodium methanearsonate); some need to be applied at a very early weed growth stage in order to completely control the infestation, i.e. the first to fourth leaf stage, for example, dithiopyr (S,S'-dimethyl 2-(difluoromethyl)-4-isobutyl-6-trifluoromethylpyridine-3,5-dicarbothiolate); and others injure or turn turf grasses yellow after application, for example, fenoxaprop ((+/−)-ethyl 2-[4[(6-chloro-2-benzoxaolyl)oxy]phenoxy}propanoate) and quinclorac (3,7-dichloro-8-quinolinecarboxylic acid). Herbicides such as quinclorac do not adequately control crabgrass in the early tiller stage of growth.

It would be most beneficial to provide a post-emergence turf herbicide that controlled weeds such as crabgrass, clover, nutsedge and violets in one application, at any weed growth stage, and without injury to turf grasses.

SUMMARY OF THE INVENTION

In accordance with the present invention, it has been found that an herbicidal composition comprising a mixture of sulfentrazone, the common name for N-[2,4-dichloro-5-[4-(difluoromethyl)-4,5-dihydro-3-methyl-5-oxo- 1H- 1,2,4-triazol-1-yl]phenyl]methanesulfonamide and quinclorac, the common name for 3,7-dichloro-8-quinolinecarboxylic acid wherein the composition is present in an herbicidally effective amount, has unexpected post-emergence control of certain broadleaf, nutsedge and grass weeds in turf sites.

DETAILED DESCRIPTION OF THE INVENTION

The present invention provides a method for post-emergence control of broadleaf, nutsedge and grass weeds in a turf site, said method comprising applying a composition comprising a mixture of sulfentrazone and quinclorac in a ratio of from 1:5 to 1:1, at a use rate of from 0.375 pound of sulfentrazone and quinclorac/acre to 1.5 pounds of sulfentrazone and quinclorac/acre, provided that the amount of sulfentrazone applied is equal to at least 0.09 lb/acre.

It has been unexpectedly found that an herbicidal composition comprising a mixture of sulfentrazone and quinclorac has advantageous properties in selective weed control over the individual components, for example the mixture controls post-emergent weeds such as crabgrass, nutsedge, violet, clover, chickweed, sesbania, jimsonweed, kochia, morningglory and pigweed, at rates which neither component alone can do. A preferred embodiment of this invention is a method for controlling 1 to 5 leaf or tillered crabgrass and nutsedge.

The terms "weed" and "weeds" refer to any unwanted vegetation in turf sites. The terms "turf", "turf site" and "turf sites" refers to, but is not limited to, residential and institutional lawns, athletic fields, parks, commercial sod farms and golf course fairways and roughs.

The structural formula of 3,7-dichloro-8-quinolinecarboxylic acid is as follows:

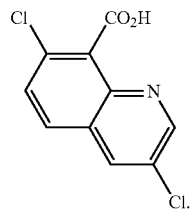 [SMILES: O=C(O)c1c(Cl)ccc2cc(Cl)cnc12]

This material, commonly known as quinclorac, is a post-emergence turf herbicide which controls a number of grass and broadleaf weeds.

The structural formula for N-[2,4-dichloro-5-[4-(difluoromethyl)-4,5-dihydro-3-methyl-5-oxo- 1H-1,2,4-triazol-1-yl]phenyl]methanesulfonamide is as follows:

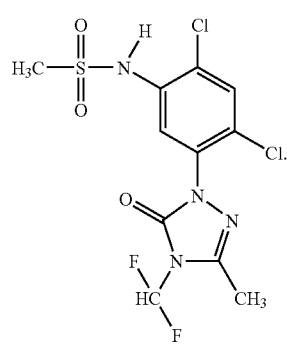 [SMILES: Cc1nn(-c2cc(NS(C)(=O)=O)c(Cl)cc2Cl)c(=O)n1C(F)F]

This material, commonly known as sulfentrazone, is a post-emergence turf herbicide which does not control crabgrass.

In the present invention, the herbicidal composition is a mixture of sulfentrazone and quinclorac in a ratio of from 1:5 to 1:1, preferably in a ratio of 1:3. The herbicidal composition of the present invention is applied at a use rate in which sulfentrazone would be present at a minimum of 0.09 lb/acre. The preferred use rate of the present herbicidal composition is from 0.375 pound of active ingredients/acre (i.e. a 1:3 ratio would contain 0.09 lb/acre of sulfentrazone and 0.28 lb/acre of quinclorac) to 1.5 pounds of active ingredients/acre (i.e. a 1:3 ratio would contain 0.375 lb/acre of sulfentrazone and 1.125 lb/acre of quinclorac).

A particular embodiment of the present invention is a method for controlling broadleaf, sedge and grass weeds in turf sites which comprises applying the present composition of sulfentrazone and quinclorac, either together or sequentially, to a locus where weeds are present.

Other herbicides can be employed in conjunction with the first and second herbicides described above providing they do not adversely affect the interaction between the components of this invention. For example it can sometimes be useful to include additional herbicides to extend the range of activity in order to control a wider spectrum of weeds.

The herbicidal compounds of use in the present invention may be employed in many forms and are often most conveniently prepared in aqueous form immediately prior to use. One method of preparing such a composition is referred to as "tank mixing" in which the ingredients in their commercially available form, either with or without other additives, are mixed together by the user in a quantity of water.

In addition to tank mixing immediately prior to use, the composition containing sulfentrazone and quinclorac may be formulated into a more concentrated primary composition which is diluted with water or other diluent before use. Such compositions may comprise a surface active agent in addition to the active ingredients and examples of such compositions are set forth below.

The herbicidal compounds of use in the present invention can be formulated as a granule of relatively large particle size for dry application to the site where control is desired (for example, 8/16 or 4/8 US Mesh), on fertilizer granules, as water-soluble or water-dispersible granules, as powdery dusts, as wettable powders, as emulsifiable concentrates, as aqueous emulsions, as solutions, or as any of the other known types of agriculturally-useful formulations, depending on the desired mode of application to the areas in which suppression of vegetation is desired. These formulations may contain as little as 0.1%, 0.2% or 0.5% to as much as 95% or more by weight of the total of the two herbicides.

The herbicidal compounds of use in the present invention can be in the form of a dispersible solution which comprises the herbicides dissolved in a water-miscible solvent with the addition of a dispersing agent.

Alternatively, the composition can be in the form of water-soluble or water-dispersible granules that disperse readily in water or other dispersant. Water-soluble or water-dispersible granules normally are prepared to contain about 5-80% of the herbicides, depending on the absorbency of the carrier, and usually also contain a wetting, dispersing or emulsifying agent to facilitate dispersion and may contain a preservative. Typical carriers for water-soluble or water-dispersible granules include Fuller's earth, natural clays, silicas, and other highly absorbent, readily wet inorganic diluents. For example, a useful water-soluble or water-dispersible granule formulation contains 26.71 parts of the herbicidal compounds, 30.90 parts of ammonium sulfate, 30.89 parts of continental clay, 10.00 parts of sodium lignosulfonate as a dispersant, 1.00 part of sodium dioctylsuccinate as a wetting agent and 0.50 part of citric acid as a preservative. The mixture is milled, diluted with water to form a paste and the paste is extruded and dried to produce granules.

Other alternatives that may be employed are dusts which are free flowing admixtures of the herbicides with finely divided solids such as talc, natural clays, kieselguhr, flours such as walnut shell and cottonseed flours, and other organic and inorganic solids which act as dispersants and carriers for the herbicides. These finely divided solids have an average particle size of less than about 50 microns. A typical dust formulation useful herein is one containing 1.0 part or less of the herbicidal compounds and 99.0 parts of talc.

Also useful formulations for the herbicidal compounds of use in the present invention are wettable powders in the form of finely divided particles that disperse readily in water or other dispersant. The wettable powder is ultimately applied to the locus where weed control is needed either as a dry dust or as an emulsion in water or other liquid. Typical carriers for wettable powders include Fuller's earth, kaolin clays, silicas, and other highly absorbent, readily wet inorganic diluents. Wettable powders are prepared to contain about 5-80% of the herbicides, depending on the absorbency of the carrier, and usually also contain a small amount of a wetting, dispersing or emulsifying agent to facilitate dispersion. For example, a useful wettable powder formulation contains 80.0 parts of the herbicidal compounds, 17.9 parts of Palmetto clay, and 1.0 part of sodium lignosulfonate and 0.3 part of sulfonated aliphatic polyester as wetting agents. Additional wetting agents and/or oils will frequently be added to a tank mix to facilitate dispersion on the foliage of the plant. Dry flowable formulations (DF) are useful formulation for herbicidal compounds. A DF formulation can be prepared by forming a paste from a wettable powder by adding a liquid, for example, water, then extruding the paste and drying to form small dustless granules.

Other useful formulations for the herbicidal compounds of use in the present invention are emulsifiable concentrates (ECs) which are homogeneous liquid compositions dispersible in water or other dispersant, and may consist entirely of the herbicidal compounds and a liquid or solid emulsifying agent, or may also contain a liquid carrier, such as xylene, heavy aromatic naphthas, isophorone, or other non-volatile organic solvents. For herbicidal application these concentrates are dispersed in water or other liquid carriers and applied as a spray to the area to be treated. The percentage by weight of the herbicidal compounds may vary according to the manner in which the composition is to be applied, but in general comprises 0.5 to 95% of the herbicidal compounds by weight of the total composition.

Suspension concentrate (SC) formulations may also be employed. These are similar to ECs, except that the herbicidal compounds are suspended in a liquid carrier, generally water. Suspension concentrate formulations, like ECs, may include small amounts of surfactants, emulsifiers, stabilizers, thickeners, antifoam agents and/or preservatives and will typically contain the herbicidal compounds in the range of 0.5 to 95%, frequently from 10 to 50%, by weight of the total composition. For herbicidal application, SCs may be diluted in water or other liquid vehicle, and are normally applied as a spray to the area to be treated.

Other useful formulations include suspensions of the herbicidal compounds in a relatively non-volatile solvent such as water, corn oil, kerosene, propylene glycol, or other suitable solvents.

Still other useful formulations for these herbicidal compositions include simple solutions of the herbicides in a solvent in which it is completely soluble at the desired concentration, such as acetone, alkylated naphthalenes, xylene, or other organic solvents. Granular formulations, wherein the herbicides are carried on relative coarse particles, are of particular utility for application to turf sites by a spreader for penetration of grass or can be used in combination with a solid fertilizer to combine nutrition and weed control. Pressurized sprays, typically aerosols wherein the herbicides are dispersed in finely divided form as a result of vaporization of a low-boiling dispersant solvent carrier may also be used.

In some circumstances it may be desirable to combine two types of formulation e.g. one of the herbicidal compounds is used as an emulsifiable concentrate and the second herbicidal compound is dispersed as a powder in this concentrate.

The concentrate of the first and second herbicides (when used as the sole active components) in a composition for direct application to the locus where control is desired by conventional ground methods is preferably within the range of 0.001 to 10% by weight of the composition, especially 0.005 to 5% by weight, but more concentrated compositions containing up to 40% may be desirable.

Typical wetting, dispersing or emulsifying agents that may be used in the compositions of the present invention include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. Surface-active agents, when used, normally comprise 1 to 15% by weight of the composition.

In use on turf sites, the granular formulations, emulsifiable concentrates, flowable concentrates, aqueous emulsions, solutions, etc., may be diluted with water to give a concentration of the active ingredient in the range of 0.01% or 0.2% to 1.5% or 2.0%.

The following examples further illustrate the present invention, but, of course, should not be construed as in any way limiting its scope. The examples include protocols for the evaluation of the compositions of the present invention in which a beneficial effect was observed. The test compositions used were formulated pre-mixes or commercially available formulations of the test compounds. The following commercially available formulations were used: sulfentrazone, DISMISS™ Turf Herbicide from FMC Corporation; quinclorac, FACET® 75 DF herbicide or DRIVE® 75DF Herbicide from BASF Corporation, Inc.

A 75 DF formulation of sulfentrazone was prepared containing the following: 81.6 parts of sulfentrazone technical (92% active), 4.0 parts sodium diisopropyl naphthalene sulfonate, 12.0 parts lignosulfonate dispersants and 2.4 parts attaclay.

A mixture of sulfentrazone and quinclorac in a 1:3 ratio was prepared by blending together 60.02 grams of a 75 DF formulation of sulfentrazone with 180.03 grams of Facet® 75 DF herbicide.

EXAMPLE 1

Post-emergent Herbicidal Evaluation of Sulfentrazone, Quinclorac and a One to Three Mixture of Sulfentrazone and Quinclorac on 3 Leaf/2 Tiller Crabgrass, Violet, Clover and Plaintain The compositions of the present invention were tested for herbicidal efficacy in the following manner:

The experimental design used randomized plots with post-emergent treatment and three replications per test trial. The size of each experimental plot was 4 feet by 6 feet. The application of each test composition was performed with pressurized back-pack sprayers, calibrated to spray 200 gallons per acre. Test compositions containing sulfentrazone (DISMISS™ Turf Herbicide), quniclorac, (FACET® 75 DF herbicide) or a mixture of sulfentrazone and quinclorac in a 1:3 ratio, prepared as described above, were diluted with water to provide the appropriate test rate concentrations.

The control of weeds was evaluated in each experimental plot from 7 to 41 days after treatment (DAT) of each test rate. The results, shown as an average of the replications, were compared with results observed in untreated control plots in the same trials. The results are in Table 1 below.

TABLE 1

Percent Control of Weeds in Turf Grass (three replications)

| Treatment | Rate of Appln. (lb ai/acre) | 7 DAT | 14 DAT | 21 DAT | 28 DAT | 41 DAT |
|---|---|---|---|---|---|---|
| Smooth Crabgrass (*Digitaria ischaemum*) | | | | | | |
| A | 0.57 | 70 | 78 | 86 | 75 | 71 |
| B | 0.75 | 75 | 55 | 78 | 67 | 57 |
| C | 1.0 | 75 | 86 | 89 | 92 | 93 |
| Control | — | 0 | 0 | 0 | 0 | 0 |
| Field Violet (*Viola arvensis*) | | | | | | |
| A | 0.57 | 64 | 75 | 76 | 70 | 75 |
| B | 0.75 | 43 | 46 | 43 | 41 | 37 |
| C | 1.0 | 76 | 71 | 72 | 89 | 89 |
| Control | — | 0 | 0 | 0 | 0 | 0 |
| White Clover (*Trifolium repens*) | | | | | | |
| A | 0.57 | 59 | 63 | 59 | 52 | — |
| B | 0.75 | 50 | 50 | 50 | 63 | — |
| C | 1.0 | 63 | 79 | 100 | 89 | — |
| Control | — | 0 | 0 | 0 | 0 | — |
| Yellow Nutsedge (*Cyperus esculentus*) | | | | | | |
| A | 0.57 | 50 | 75 | 89 | 91 | — |
| B | 0.75 | 100 | 40 | 10 | 13 | — |
| C | 1.0 | 95 | 100 | 100 | 100 | — |
| Control | — | 0 | 0 | 0 | 0 | — |
| Blackseed Plantain (*Plantago rugelii*) | | | | | | |
| A | 0.57 | 83 | 88 | 100 | 100 | — |
| B | 0.75 | 100 | 100 | 100 | 100 | — |
| C | 1.0 | 100 | 100 | 100 | 100 | — |
| Control | — | 0 | 0 | 0 | 0 | — |

Highlighted numbers indicate advantageous herbicidal properties.
A = sulfentrazone, DISMISS ™ Turf Herbicide available from FMC Corporation
B = quinclorac, FACET ® 75 DF herbicide from BASF Corporation, Inc.
C = sulfentrazone/quinclorac 1:3 ratio (1.0 lb/acre = 0.25 lb/acre sulfentrazone, 0.75 lb/acre quinclorac)

EXAMPLE 2

Post-emergent Herbicidal Evaluation of Sulfentrazone, Quinclorac and a One to Three Mixture of Sulfentrazone and Quinclorac on Tillered Crabgrass, Violet, Clover, Nutsedge and Plaintain The compositions of the present invention were tested for herbicidal efficacy in the following manner:

The experimental design used randomized plots with post-emergent treatment and three replications per test trial. The size of each experimental plot was 4 feet by 6 feet. The application of each test composition was performed with pressurized back-pack sprayers, calibrated to spray 200 gallons per acre. Test compositions containing sulfentrazone (DISMISS™ Turf Herbicide), quinclorac, (FACET® 75 DF herbicide) or a mixture of sulfentrazone and quinclorac in a one to three ratio, prepared as described above, were diluted with water to provide the appropriate test rate concentrations.

The control of weeds was evaluated in each experimental plot from 1 to 27 days after treatment (DAT) of each test rate. The results, shown as an average of the replications, were compared with results observed in untreated control plots in the same trials. The results are in Table 2 below.

TABLE 2

Percent Control of Weeds in Turf Grass
(three replications)

| Treatment | Rate of Appln. (lb ai/acre) | 7 DAT | 14 DAT | 21 DAT |
|---|---|---|---|---|
| Smooth Crabgrass (*Digitaria ischaemum*) | | | | |
| A | 0.57 | 34 | 36 | 52 |
| B | 0.75 | 54 | 66 | 67 |
| C | 1.0 | 80 | 85 | 88 |
| Control | — | 0 | 0 | 0 |
| Field Violet (*Viola arvensis*) | | | | |
| A | 0.57 | 66 | 78 | 69 |
| B | 0.75 | 46 | 48 | 51 |
| C | 1.0 | 66 | 91 | 89 |
| Control | — | 0 | 0 | 0 |
| White Clover (*Trifolium repens*) | | | | |
| A | 0.57 | 45 | 74 | 68 |
| B | 0.75 | 60 | 87 | 82 |
| C | 1.0 | 66 | 96 | 96 |
| Control | — | 0 | 0 | 0 |
| Yellow Nutsedge (*Cyperus esculentus*) | | | | |
| A | 0.57 | 100 | 100 | 100 |
| B | 0.75 | 83 | 54 | 37 |
| C | 1.0 | 100 | 100 | 100 |
| Control | — | 0 | 0 | 0 |
| Blackseed Plantain (*Plantago rugelii*) | | | | |
| A | 0.57 | 100 | 100 | 100 |
| B | 0.75 | 83 | 100 | 100 |
| C | 1.0 | 100 | 100 | 100 |
| Control | — | 0 | 0 | 0 |

Highlighted numbers indicate advantageous herbicidal properties.
A = sulfentrazone, DISMISS ™ Turf Herbicide available from FMC Corporation
B = quinclorac, FACET ® 75 DF herbicide from BASF Corporation, Inc.
C = sulfentrazone/quinclorac 1:3 ratio (1.0 lb/acre = 0.25 lb/acre sulfentrazone, 0.75 lb/acre quinclorac)

EXAMPLE 3

Post-emergent herbicidal evaluation of Sulfentrazone, Quinclorac and a One to Three Mixture of Sulfentrazone and Quinclorac On Crabgrass and Yellow Nutsedge The compositions of the present invention were tested for herbicidal efficacy in the following manner:

Test compositions containing sulfentrazone (DISMISS™ Turf Herbicide), quniclorac, (DRIVE® 75 DF Herbicide) or mixture of sulfentrazone and quinclorac in a three to one ratio, prepared as described above, were diluted with water to provide the appropriate test rate concentrations. A nonionic surfactant (0.25%) was added to each test solution.

The test weeds include Red River crabgrass (*Digitaria ciliaris*) and yellow nutsedge (*Cyperus esculentusi*).

For post-emergence testing, three disposable 3 inch square pots for each rate of application of each herbicide were filled with a soil, comprised of peat moss, vermiculite, bark ash, pine bark, limestone and a wetting agent, to which 8 to 10 seeds were planted. The pots were placed in a greenhouse and watered daily, thus allowing the seeds to germinate and the foliage to develop.

Pots designated for treatment were placed on a conveyor belt and the conveyor belt fed under a spray nozzle mounted about ten inches above the foliage. The spray of herbicidal solution was commenced and once stabilized; the pots were passed under the spray at a speed to receive a coverage equivalent of 30 gallons per acre. The application rates are those shown in Table 3 below for the individual herbicidal solutions and the mixture of sulfentrazone and quinclorac. The post-emergence pots were immediately placed in the green-house and not watered until 24 hours after treatment with the test solution. Thereafter they were regularly watered at ground level. The control of weeds was evaluated in each experimental test from 1 to 22 days after treatment (DAT). The results, shown as an average of the replications, were compared with results observed in untreated control pots in the same tests. The results are in Table 3 below.

Percent control was determined by a method similar to the 0 to 100 rating system disclosed in "Research Methods in Weed Science," 2nd ed., B. Truelove, Ed.; Southern Weed Science Society; Auburn University, Auburn, Ala., 1977. The rating system is as follows:

| Herbicide Rating System | | |
|---|---|---|
| Rating Percent Control | Description of Main Categories | Weed Description |
| 0 | No Effect | No weed control |
| 10 | | Very poor weed control |
| 20 | Slight Effect | Poor weed control |
| 30 | | Poor to deficient weed control |
| 40 | | Deficient weed control |
| 50 | Moderate Effect | Deficient to moderate weed control |
| 60 | | Moderate weed control |
| 70 | | Control somewhat less than satisfactory |
| 80 | Severe | Satisfactory to good weed control |
| 90 | | Very good to excellent weed control |
| 100 | Complete Effect | Complete weed destruction |

TABLE 3

Percent Control of Red River Crabgrass (*Digitaria ciliaris*) and Yellow Nutsedge (*Cyperus esculentusi*)
(three replications)

| Treatment | Rate of Appln. (lb ai/acre) | 1 DAT | 3 DAT | 7 DAT | 14 DAT | 21 DAT |
|---|---|---|---|---|---|---|
| Red River Crabgrass Treated at 1-2 leaf stage, 11 days old | | | | | | |
| A | 0.375 | 50 | 70 | 50 | 20 | 10 |
| A | 0.25 | 60 | 70 | 50 | 20 | 5 |

TABLE 3-continued

Percent Control of Red River Crabgrass (*Digitaria ciliaris*) and Yellow Nutsedge (*Cyperus esculentusi*)
(three replications)

| Treatment | Rate of Appln. (lb ai/acre) | 1 DAT | 3 DAT | 7 DAT | 14 DAT | 21 DAT |
|---|---|---|---|---|---|---|
| A | 0.125 | 50 | 60 | 50 | 40 | 30 |
| B | 1.0 | 0 | 10 | 10 | 2 | 2 |
| B | 0.75 | 0 | 10 | 5 | 0 | 0 |
| B | 0.375 | 0 | 5 | 5 | 0 | 0 |
| C | 1.5 | 50 | 70 | 75 | 80 | 80 |
| C | 1.25 | 50 | 70 | 75 | 72 | 75 |
| C | 1.0 | 47 | 60 | 70 | 67 | 74 |
| C | 0.75 | 60 | 60 | 75 | 70 | 70 |
| C | 0.375 | 53 | 60 | 50 | 43 | 40 |
| Control | — | 0 | 0 | 0 | 0 | 0 |
| Red River Crabgrass Treated at 3-4 leaf stage, 1-2 tillers, 14 days old | | | | | | |
| A | 0.375 | 20 | 20 | 22 | 0 | 0 |
| A | 0.25 | 25 | 25 | 30 | 12 | 5 |
| A | 0.125 | 25 | 25 | 30 | 10 | 5 |
| B | 1.0 | 0 | 5 | 10 | 5 | 5 |
| B | 0.75 | 0 | 5 | 5 | 5 | 0 |
| B | 0.375 | 0 | 5 | 5 | 0 | 0 |
| C | 1.5 | 20 | 60 | 75 | 77 | 75 |
| C | 1.25 | 20 | 60 | 75 | 72 | 75 |
| C | 1.0 | 15 | 60 | 75 | 70 | 60 |
| C | 0.75 | 15 | 60 | 70 | 63 | 60 |
| C | 0.375 | 20 | 60 | 70 | 67 | 50 |
| Control | — | 0 | 0 | 0 | 0 | 0 |
| Yellow Nutsedge, Treated at 1-5 leaf stage, 7 days old | | | | | | |
| A | 0.375 | 75 | 91 | 95 | 73 | 70 |
| A | 0.25 | 70 | 85 | 77 | 68 | 50 |
| A | 0.125 | 50 | 50 | 63 | 70 | 67 |
| B | 1.0 | 0 | 0 | 0 | 0 | 0 |
| B | 0.75 | 0 | 0 | 0 | 0 | 0 |
| B | 0.375 | 0 | 0 | 0 | 0 | 0 |
| C | 1.5 | 40 | 94 | 98 | 90 | 85 |
| C | 1.25 | 40 | 85 | 96 | 95 | 80 |
| C | 1.0 | 40 | 77 | 80 | 87 | 80 |
| C | 0.75 | 50 | 88 | 87 | 77 | 70 |
| C | 0.375 | 40 | 87 | 82 | 63 | 70 |
| Control | — | 0 | 0 | 0 | 0 | 0 |
| Yellow Nutsedge Treated at 5-7 leaves, cut to 6 cm tall, 28 days old | | | | | | |
| A | 0.375 | 0 | 90 | 90 | 90 | 90 |
| A | 0.25 | 0 | 75 | 80 | 80 | 90 |
| A | 0.125 | 0 | 80 | 85 | 70 | 60 |
| B | 1.0 | 0 | 5 | 5 | 5 | 0 |
| B | 0.75 | 0 | 0 | 2 | 2 | 0 |
| B | 0.375 | 0 | 5 | 5 | 5 | 0 |
| C | 1.5 | 0 | 80 | 85 | 85 | 50 |
| C | 1.25 | 0 | 80 | 85 | 85 | 90 |
| C | 1.0 | 0 | 70 | 90 | 90 | 90 |
| C | 0.75 | 0 | 70 | 90 | 90 | 90 |
| C | 0.375 | 0 | 70 | 90 | 70 | 70 |
| Control | — | 0 | 0 | 0 | 0 | |

Highlighted numbers indicate advantageous herbicidal properties.
A = sulfentrazone, DISMISS ™ Turf Herbicide available from FMC Corporation
B = quinclorac, DRIVE ® 75 DF herbicide from BASF Corporation, Inc.
C = sulfentrazone/quinclorac 1:3 ratio (1.0 lb/acre = 0.25 lb/acre sulfentrazone, 0.75 lb/acre quinclorac)

EXAMPLE 4

Post-Emergent Hebicidal Evaluation of Sulfentrazone, Quinclorac and Mixtures of Sulfentrazone and Quinclorac The compositions of the present invention were tested for herbicidal efficacy in the following manner:

Test compositions containing sulfentrazone (75 DF formulation), quniclorac, (DRIVE® 75 DF Herbicide) or mixtures of sulfentrazone and quinclorac at ratios of 1:1 to 1:5, were diluted with water to provide the appropriate test rate concentrations. A nonionic surfactant (0.25%) was added to each test solution.

The test weeds include crabgrass (*Digitaria* sp), Chickweed (*Stellaria media*), Hemp Sesbania (*Sesbania exaltata*), Kochia (*Kochia scoparia*), Ivyleaf Momingglory (*Ipomoea hederacea*), Redroot Pigweed (*Amaranthus retroflexus*) and yellow nutsedge (*Cyperus esculentusi*).

For post-emergence testing, three disposable 3 inch square pots for each rate of application of each herbicide were filled with a soil, comprised of peat moss, vermiculite, bark ash, pine bark, limestone and a wetting agent, to which 8 to 10 seeds were planted. The pots were placed in a greenhouse and watered daily, thus allowing the seeds to germinate and the foliage to develop for 22 days, 3 months for Kochia.

Pots designated for treatment were placed on a conveyor belt and the conveyor belt fed under a spray nozzle mounted about ten inches above the foliage. The spray of herbicidal solution was commenced and once stabilized; the pots were passed under the spray at a speed to receive a coverage equivalent of 30 gallons per acre. The application rates are those shown in Table 4 below for the individual herbicidal solutions and the mixture of sulfentrazone and quinclorac. The post-emergence pots were immediately placed in the green-house and not watered until 24 hours after treatment with the test solution. Thereafter they were regularly watered at ground level. The control of weeds was evaluated in each experimental test from 2 to 20 days after treatment (DAT). The results, shown as an average of the replications, were compared with results observed in untreated control pots in the same tests. The results are in Table 4 below.

Percent control was determined by a method similar to the 0 to 100 rating system disclosed in "Research Methods in Weed Science," 2nd ed., B. Truelove, Ed.; Southern Weed Science Society; Auburn University, Auburn, Ala., 1977. The rating system is as follows:

| Herbicide Rating System | | |
|---|---|---|
| Rating Percent Control | Description of Main Categories | Weed Description |
| 0 | No Effect | No weed control |
| 10 | | Very poor weed control |
| 20 | Slight Effect | Poor weed control |
| 30 | | Poor to deficient weed control |
| 40 | | Deficient weed control |
| 50 | Moderate Effect | Deficient to moderate weed control |
| 60 | | Moderate weed control |
| 70 | | Control somewhat less than satisfactory |
| 80 | Severe | Satisfactory to good weed control |
| 90 | | Very good to excellent weed control |
| 100 | Complete Effect | Complete weed destruction |

TABLE 4

Post-emergent Herbicidal Evaluation of Sulfentrazone, Quinclorac and Mixtures Thereof

| Treatment | Rate of application (lb ai/acre) | 2 DAT | 7 DAT | 14 DAT | 20 DAT |
|---|---|---|---|---|---|
| Crabgrass | | | | | |
| A | 0.25 | 10 | 10 | 5 | 5 |
| B | 0.25 | 10 | 20 | 20 | 10 |
| B | 0.5 | 0 | 10 | 60 | 50 |
| B | 0.75 | 0 | 0 | 60 | 50 |
| B | 1.0 | 0 | 10 | 60 | 70 |
| B | 1.25 | 0 | 10 | 60 | 70 |
| A/B | 0.25/0.25 | 10 | 10 | 10 | 10 |
| A/B | 0.25/0.5 | 10 | 10 | 70 | 60 |
| A/B | 0.25/0.75 | 15 | 10 | 75 | 60 |
| A/B | 0.25/1.0 | 10 | 10 | 70 | 75 |
| A/B | 0.25/1.25 | 10 | 10 | 75 | 80 |
| Control | 0 | 0 | 0 | 0 | 0 |
| Chickweed | | | | | |
| A | 0.25 | 30 | 30 | 10 | 0 |
| B | 0.25 | 0 | 0 | 0 | 0 |
| B | 0.5 | 0 | 0 | 0 | 0 |
| B | 0.75 | 0 | 0 | 0 | 0 |
| B | 1.0 | 0 | 5 | 5 | 5 |
| B | 1.25 | 5 | 5 | 2 | 5 |
| A/B | 0.25/0.25 | 10 | 40 | 50 | 20 |
| A/B | 0.25/0.5 | 10 | 60 | 60 | 60 |
| A/B | 0.25/0.75 | 15 | 40 | 50 | 50 |
| A/B | 0.25/1.0 | 10 | 40 | 50 | 50 |
| A/B | 0.25/1.25 | 10 | 40 | 60 | 40 |
| Control | 0 | 0 | 0 | 0 | 0 |
| Hemp Sesbania | | | | | |
| A | 0.25 | 70 | 85 | 90 | 90 |
| B | 0.25 | 0 | 0 | 5 | 20 |
| B | 0.5 | 0 | 10 | 20 | 60 |
| B | 0.75 | 0 | 0 | 10 | 60 |
| B | 1.0 | 10 | 10 | 20 | 60 |
| B | 1.25 | 0 | 0 | 10 | 50 |
| A/B | 0.25/0.25 | 75 | 75 | 90 | 95 |
| A/B | 0.25/0.5 | 70 | 75 | 99 | 99 |
| A/B | 0.25/0.75 | 60 | 60 | 90 | 90 |
| A/B | 0.25/1.0 | 50 | 60 | 95 | 99 |
| A/B | 0.25/1.25 | 50 | 70 | 95 | 99 |
| Control | 0 | 0 | 0 | 0 | 0 |
| Kochia | | | | | |
| A | 0.25 | 10 | 70 | 95 | 99 |
| B | 0.25 | 0 | 0 | 5 | 5 |
| B | 0.5 | 0 | 0 | 20 | 20 |
| B | 0.75 | 0 | 0 | 10 | 5 |
| B | 1.0 | 0 | 0 | 10 | 20 |
| B | 1.25 | 0 | 0 | 10 | 10 |
| A/B | 0.25/0.25 | 10 | 85 | 100 | 100 |
| A/B | 0.25/0.5 | 10 | 75 | 99 | 100 |
| A/B | 0.25/0.75 | 10 | 75 | 99 | 100 |
| A/B | 0.25/1.0 | 10 | 50 | 90 | 100 |
| A/B | 0.25/1.25 | 10 | 70 | 99 | 100 |
| Control | 0 | 0 | 0 | 0 | 0 |
| Ivyleaf Morningglory | | | | | |
| A | 0.25 | 60 | 80 | 90 | 99 |
| B | 0.25 | 20 | 25 | 60 | 70 |
| B | 0.5 | 20 | 25 | 40 | 50 |
| B | 0.75 | 20 | 25 | 40 | 50 |
| B | 1.0 | 20 | 25 | 50 | 70 |
| B | 1.25 | 20 | 25 | 40 | 50 |
| A/B | 0.25/0.25 | 70 | 95 | 99 | 100 |
| A/B | 0.25/0.5 | 80 | 100 | 100 | 100 |
| A/B | 0.25/0.75 | 70 | 100 | 100 | 100 |
| A/B | 0.25/1.0 | 60 | 95 | 100 | 100 |
| A/B | 0.25/1.25 | 60 | 100 | 100 | 100 |
| Control | 0 | 0 | 0 | 0 | 0 |
| Redroot Pigweed | | | | | |
| A | 0.25 | 80 | 95 | 99 | 90 |
| B | 0.25 | 10 | 10 | 10 | 10 |
| B | 0.5 | 0 | 0 | 0 | 0 |
| B | 0.75 | 0 | 0 | 0 | 0 |
| B | 1.0 | 0 | 0 | 0 | 0 |
| B | 1.25 | 10 | 10 | 10 | 10 |
| A/B | 0.25/0.25 | 80 | 95 | 99 | 95 |
| A/B | 0.25/0.5 | 80 | 100 | 100 | 100 |
| A/B | 0.25/0.75 | 50 | 99 | 100 | 100 |
| A/B | 0.25/1.0 | 70 | 100 | 100 | 95 |
| A/B | 0.25/1.25 | 70 | 100 | 100 | 100 |
| Control | 0 | 0 | 0 | 0 | 0 |
| Yellow Nutsedge | | | | | |
| A | 0.25 | 25 | 60 | 85 | 95 |
| B | 0.25 | 0 | 0 | 0 | 0 |
| B | 0.5 | 0 | 0 | 0 | 0 |
| B | 0.75 | 0 | 0 | 0 | 0 |
| B | 1.0 | 0 | 0 | 0 | 0 |
| B | 1.25 | 0 | 0 | 0 | 0 |
| A/B | 0.25/0.25 | 25 | 75 | 90 | 90 |
| A/B | 0.25/0.5 | 30 | 60 | 80 | 99 |
| A/B | 0.25/0.75 | 20 | 70 | 90 | 95 |
| A/B | 0.25/1.0 | 30 | 50 | 75 | 90 |
| A/B | 0.25/1.25 | 30 | 60 | 85 | 95 |
| Control | 0 | 0 | 0 | 0 | 0 |

Highlighted numbers indicate advantageous herbicidal properties.
A = sulfentrazone, 75 DF formulation.
B = quinclorac, DRIVE ® 75 DF herbicide from BASF Corporation, Inc.

Those of ordinary skill in the art will appreciate that variations of the invention may be used and that it is intended that the invention may be practiced otherwise than as specifically described herein. Accordingly, this invention includes all modifications encompassed within the spirit and scope of the invention as defined by the following claims.

What is claimed is:

1. A method for post-emergence control of crabgrass in a turf site, said method comprising applying a composition comprising a mixture of sulfentrazone and quinclorac in a ratio of from 1:5 to 1:1 at a rate of from 0.375 pound of sulfentrazone and quinclorac/acre to 1.5 pounds of sulfentrazone and quinclorac/acre, provided that the amount of sulfentrazone applied is equal to at least 0.09 lb/acre.

2. The method of claim 1 wherein the ratio of sulfentrazone to quinclorac is 1:3.

3. The method of claim 2 wherein the mixture of sulfentrazone and quinclorac is applied at a rate of from 0.75 pound of sulfentrazone and quinclorac/acre to 1.25 pounds of sulfentrazone and quinclorac/acre.

\* \* \* \* \*